(12) United States Patent
Wilk

(10) Patent No.: US 6,302,892 B1
(45) Date of Patent: Oct. 16, 2001

(54) BLOOD FLOW CONDUIT DELIVERY SYSTEM AND METHOD OF USE

(75) Inventor: Peter J. Wilk, New York, NY (US)

(73) Assignee: Percardia, Inc., Nashua, NH (US)

( * ) Notice: Subject to any disclaimer, the term of this patent is extended or adjusted under 35 U.S.C. 154(b) by 0 days.

(21) Appl. No.: 09/368,644

(22) Filed: Aug. 4, 1999

(51) Int. Cl.[7] .................................................. A61F 11/00
(52) U.S. Cl. ........................................... 606/108; 128/898
(58) Field of Search .................................... 606/108, 194, 606/195, 198; 623/1.11; 128/898; 604/96.01, 164.01, 528

(56) References Cited

U.S. PATENT DOCUMENTS

| | | | |
|---|---|---|---|
| 4,503,568 | * 3/1985 | Madras . | |
| 4,665,918 | * 5/1987 | Garza et al. | 128/343 |
| 5,122,154 | * 6/1992 | Rhodes | 606/198 |
| 5,190,058 | 3/1993 | Jones et al. . | |
| 5,258,008 | 11/1993 | Wilk . | |
| 5,287,861 | 2/1994 | Wilk . | |
| 5,316,023 | * 5/1994 | Palmaz et al. | 128/898 |
| 5,330,486 | 7/1994 | Wilk . | |
| 5,409,019 | 4/1995 | Wilk . | |
| 5,429,144 | 7/1995 | Wilk . | |
| 5,443,497 | * 8/1995 | Venbrux . | |
| 5,453,090 | * 9/1995 | Martinez et al. | 606/108 |
| 5,456,694 | 10/1995 | Marin et al. . | |
| 5,456,712 | * 10/1995 | Maginot . | |
| 5,470,320 | 11/1995 | Tifenbrun et al. . | |
| 5,549,663 | * 8/1996 | Cottone, Jr. | 606/195 |
| 5,571,167 | * 11/1996 | Maginot . | |
| 5,607,444 | * 3/1997 | Lam | 606/194 |
| 5,632,762 | * 5/1997 | Myler | 606/194 |
| 5,643,278 | 7/1997 | Wijay . | |
| 5,653,743 | * 8/1997 | Martin | 606/194 |
| 5,655,548 | 8/1997 | Nelson et al. . | |
| 5,662,124 | 9/1997 | Wilk . | |
| 5,676,670 | 10/1997 | Kim . | |
| 5,709,713 | * 1/1998 | Evans et al. | 606/198 |
| 5,733,267 | 3/1998 | Del Toro . | |
| 5,755,682 | * 5/1998 | Knudson et al. | 604/8 |
| 5,758,663 | 6/1998 | Wilk et al. . | |
| 5,797,920 | 8/1998 | Kim . | |
| 5,810,836 | 9/1998 | Hussein et al. . | |
| 5,810,871 | 9/1998 | Tuckey et al. . | |
| 5,824,040 | * 10/1998 | Cox et al. | 606/194 |
| 5,824,071 | 10/1998 | Nelson et al. . | |
| 5,830,222 | * 11/1998 | Makower . | |
| 5,878,751 | * 3/1999 | Hussein et al. . | |
| 5,904,697 | * 5/1999 | Gifford, III et al. . | |
| 5,908,028 | 1/1999 | Wilk . | |
| 5,908,029 | * 6/1999 | Knudson et al. . | |
| 5,922,022 | * 7/1999 | Nash et al. . | |
| 5,944,019 | * 8/1999 | Knudson et al. . | |
| 5,951,599 | * 9/1999 | McCrory | 606/108 |
| 5,961,548 | * 10/1999 | Shmulewitz . | |
| 5,968,093 | * 10/1999 | Kranz . | |
| 5,971,993 | 10/1999 | Hussein et al. . | |
| 5,976,153 | 11/1999 | Fischell et al. . | |
| 5,976,155 | 11/1999 | Foreman et al. . | |
| 5,976,178 | * 11/1999 | Goldsteen et al. . | |
| 5,979,455 | 11/1999 | Maginot . | |
| 5,980,530 | 11/1999 | Willard et al. . | |

(List continued on next page.)

FOREIGN PATENT DOCUMENTS

| | | |
|---|---|---|
| 0 938 870 | 9/1999 | (EP) . |
| 0 956 825 | 11/1999 | (EP) . |
| 2316322 | 10/1998 | (GB) . |
| 94/16629 | 8/1994 | (WO) . |
| 97/13463 | 4/1997 | (WO) . |
| 97/13471 | 4/1997 | (WO) . |
| 97/27893 | 8/1997 | (WO) . |
| 97/27897 | 8/1997 | (WO) . |
| 97/27898 | 8/1997 | (WO) . |
| 97/41916 | 11/1997 | (WO) . |
| 97/43961 | 11/1997 | (WO) . |

(List continued on next page.)

OTHER PUBLICATIONS

Gardner, M.D. et al., "An Experimental Anatomic Study of Indirect Myocardial Revascularization," *Journal of Surgical Research*, May 1971, vol. 11, No. 5, pp. 243–247.

Palmaz et al., "Expandable Intrahepatic Portacaval Shunt Stents: Early Experience in the Dog," *AJR*, 1985, vol. 145, pp. 821–825.

Palmaz et al., "Expandable Intrahepatic Portacavl Shunt Stents in Dogs with Chronic Portal Hypertension,"*AJR*, 1986, vol. 147, pp. 1251–54.

Richter, M.D. et al., "Transjugular Intrahepatic Portacaval Stent Shunt: Preliminary Clinical Results," *Radiology*, 1990, vol. 174, No. 3, pp. 1027–1030.

(List continued on next page.)

*Primary Examiner*—Jeffrey A. Smith
*Assistant Examiner*—Eduardo C. Robert
(74) *Attorney, Agent, or Firm*—Finnegan, Henderson, Farabow, Garrett & Dunner, L.L.P.

(57) ABSTRACT

Described herein is a catheter system for delivering an L-shaped conduit into the body of a patient between the left ventricle and coronary artery. A shunt preferably made of semirigid material is inserted into the lumen of a delivery catheter. The delivery catheter is advanced within the patient until its distal end is located adjacent to the desired insertion site, which is preferably the junction between a coronary artery and passageway formed in the myocardium between the left ventricle and coronary artery. A proximal section of the shunt is first advanced out of the delivery catheter into the myocardial passageway. A distal section of the shunt is advanced into the coronary artery, preferably by advancing the distal section of the shunt into the myocardial passageway and then pulling the distal section back into the coronary artery, or by pushing the distal section of the shunt in a folded configuration out of the delivery catheter into the coronary artery. In one embodiment, the shunt is made of a collapsible material for insertion into the delivery catheter, the shunt expanding upon removal from the delivery catheter.

57 Claims, 7 Drawing Sheets

U.S. PATENT DOCUMENTS

| | | | |
|---|---|---|---|
| 5,980,533 | * | 11/1999 | Holman . |
| 5,984,955 | * | 11/1999 | Wisselink . |
| 5,984,956 | * | 11/1999 | Tweden et al. . |
| 5,989,263 | * | 11/1999 | Shmulewitz . |
| 5,993,481 | * | 11/1999 | Marcade et al. . |
| 6,007,543 | | 12/1999 | Ellis et al. . |
| 6,016,810 | * | 1/2000 | Ravenscroft .................... 606/198 |
| 6,026,814 | * | 2/2000 | LaFontaine et al. . |
| 6,029,672 | * | 2/2000 | Vanney et al. . |
| 6,035,856 | * | 3/2000 | LaFontaine et al. . |
| 6,036,697 | | 3/2000 | DiCaprio . |
| 6,039,721 | | 3/2000 | Johnson et al. . |
| 6,042,581 | | 3/2000 | Ryan et al. . |
| 6,053,924 | | 4/2000 | Hussein et al. . |
| 6,053,942 | * | 4/2000 | Eno et al. ..................... 623/1.15 |
| 6,068,638 | * | 5/2000 | Makower ........................ 606/159 |
| 6,071,292 | * | 6/2000 | Makower et al. . |
| 6,076,529 | * | 6/2000 | Vanney et al. .................. 606/194 |
| 6,080,163 | | 6/2000 | Hussein et al. . |
| 6,081,738 | * | 6/2000 | Hinohara et al. ............... 606/185 |
| 6,092,526 | * | 7/2000 | LaFontaine et al. ............ 128/898 |
| 6,093,166 | * | 7/2000 | Knudson et al. . |
| 6,102,941 | * | 8/2000 | Tweden et al. . |
| 6,113,630 | * | 9/2000 | Vanney et al. . |
| 6,123,682 | * | 9/2000 | Knudson et al. . |
| 6,126,649 | * | 10/2000 | VanTassel et al. . |
| 6,139,541 | * | 10/2000 | Vanney et al. . |
| 6,159,225 | * | 12/2000 | Makower . |

FOREIGN PATENT DOCUMENTS

| | | |
|---|---|---|
| 98/06356 | 2/1998 | (WO) . |
| 98/08456 | 3/1998 | (WO) . |
| 98/10714 | 3/1998 | (WO) . |
| 98/16161 | 4/1998 | (WO) . |
| 98/19607 | 5/1998 | (WO) . |
| 98/44869 | 10/1998 | (WO) . |
| 98/46115 | 10/1998 | (WO) . |
| 98/46119 | 10/1998 | (WO) . |
| 98/57591 | 12/1998 | (WO) . |
| 99/08603 | 2/1999 | (WO) . |
| 99/08624 | 2/1999 | (WO) . |
| 99/17693 | 4/1999 | (WO) . |
| 99/21490 | 5/1999 | (WO) . |
| 99/22655 | 5/1999 | (WO) . |
| 99/25273 | 5/1999 | (WO) . |
| 99/36000 | 7/1999 | (WO) . |
| 99/36001 | 7/1999 | (WO) . |
| 99/38459 | 8/1999 | (WO) . |
| 99/40868 | 8/1999 | (WO) . |
| 99/48427 | 9/1999 | (WO) . |
| 99/48545 | 9/1999 | (WO) . |
| 99/49790 | 10/1999 | (WO) . |
| 99/49793 | 10/1999 | (WO) . |
| 99/49910 | 10/1999 | (WO) . |
| 99/51662 | 10/1999 | (WO) . |
| 99/52481 | 10/1999 | (WO) . |
| 99/53863 | 10/1999 | (WO) . |
| 99/55406 | 11/1999 | (WO) . |
| 99/60941 | 12/1999 | (WO) . |
| 99/62430 | 12/1999 | (WO) . |
| 00/09195 | 2/2000 | (WO) . |
| 00/12029 | 3/2000 | (WO) . |
| 00/15146 | 3/2000 | (WO) . |
| 00/15147 | 3/2000 | (WO) . |
| 00/15148 | 3/2000 | (WO) . |
| 00/15149 | 3/2000 | (WO) . |
| 00/15275 | 3/2000 | (WO) . |
| 00/18302 | 4/2000 | (WO) . |
| 00/21436 | 4/2000 | (WO) . |
| 00/21461 | 4/2000 | (WO) . |
| 00/21463 | 4/2000 | (WO) . |
| 00/24449 | 5/2000 | (WO) . |
| 00/33725 | 6/2000 | (WO) . |
| 00/41632 | 7/2000 | (WO) . |
| 00/41633 | 7/2000 | (WO) . |
| 00/45711 | 8/2000 | (WO) . |
| 00/56387 | 9/2000 | (WO) . |
| 00/57814 | 10/2000 | (WO) . |
| 00/66035 | 11/2000 | (WO) . |
| 00/71195 | 11/2000 | (WO) . |

OTHER PUBLICATIONS

Zemel, M.D. et al., "Percutaneous Transjugular Portosystemic Shunt," *JAMA*, 1991, vol. 266, No. 3, pp. 390–393.

Massimo, M.D. et al., "Myocardial Revascularization by a New Method of Carrying Blood Directly from the Left Ventricular Cavity into the Coronary Circulation," *Journal of Thoracic Surgeons*, Aug. 1997, vol. 34, No. 2, pp. 257–264.

Lary, M.D. et al., "Myocardial Revascularization Experiments Using the Epicardium," *Archives of Surgery*, Jan. 1969, vol. 98, No. 1, pp. 69–72.

Munro, M.D. et al., "The possibility of myocardial revascularization by creation of a left ventriculocoronary artery fistula," *Journal of Thoracic and Cardiovascular Surgery*, Jul. 1969, vol. 58, No. 1, pp. 25–32.

Kuzela, M.D. et al., "Experimental evaluation to direct transventircular revascularization," *The Journal of Thoracic and Cardiovascular Surgery*, Jun. 1969, vol. 57, No. 6, pp. 770–773.

Burch et al., "Surgical closure of coronary artery fistula emptying into left ventricle," *American Heart Journal*, Jan. 1980, vol. 99, No. 1, p. 133.

Anabtawi, M.D. et al., "Experimental evaluation of myocardial tunnelization as a method of myocardial revascularization," *The Journal of Thoracic and Cardiovascular Surgery*, Nov. 1969, vol. 58, No. 5, pp. 638–46.

Vineberg et al., "Rapid Development in Dogs of Intramyocardial Vascular Pathways After Implantation of Bloodless Omental Strips in the Right and left Ventricular Myocardium," *The Canadian Journal of Surgery*, vol. 11, Apr. 1998, pp. 219–29.

Tala, M.D. et al., "Reappraisal of internal mammary arterio–venous fistula in experimental myocardial revascularization," *The Journal of Cardiovascular Surgery*, 1968, pp. 201–06.

Urschel, Jr. M.D. et al., "Direct and indirect myocardial revascularization: Follow–up and appraisal," *Surgery*, Dec. 1970, pp. 1087–1100.

Tweden et al., "Ventriculocoronary Artery Bypass (VCAB), a Novel Approach to Myocardial Revascularization," #2000–4653, Feb. 2000.

* cited by examiner

BLOOD FLOW CONDUIT DELIVERY SYSTEM AND METHOD OF USE

BACKGROUND OF THE INVENTION

1. Field of the Invention

The present invention relates to the delivery of a shunt and other devices into the myocardium of a patient, and more particularly, to the delivery of a generally L-shaped shunt to provide a bypass through the myocardium from the left ventricle into a coronary artery.

2. Description of the Related Art

Coronary arteries as well as other vessels frequently become clogged with plaque that at the very least impairs the efficiency of the heart's pumping action and can lead to heart attack and death. One conventional treatment for clogged coronary or other arteries is a bypass operation wherein one or more venous segments are inserted between the aorta and the coronary artery. The inserted venous segments or transplants act as a bypass of the clogged portion of the coronary artery and thus provide for a free or unobstructed flow of blood to the heart.

Such coronary artery bypass surgery, however, is expensive, time-consuming and traumatic to the patient. Hospital stays subsequent to the surgery and convalescence are prolonged.

A new coronary artery bypass technique is disclosed in U.S. Pat. No. 5,429,144. That technique utilizes a stent made of a biocompatible material and comprises steps of moving the stent in a collapsed configuration through a blood vessel of a patient's vascular system to the patient's heart, inserting the stent in the patient's myocardium, and upon disposition of the stent in the myocardium, expanding the stent from the collapsed configuration to a substantially tubular expanded configuration so that a blood flow path is formed at least partially through the myocardium.

U.S. Pat. No. 5,755,682 to Knudson discloses an L-shaped shunt (see FIG. 1A of Knudson) having one end in the lumen of an artery facing downstream from an obstruction and the other end in fluid communication with blood within the heart chamber. One problem with using this L-shaped shunt is how to get the shunt into the myocardium without undue trauma to the patient.

SUMMARY OF THE INVENTION

The problem of delivering an L-shaped shunt or conduit is solved herein by providing an improved catheter delivery system. A shunt preferably made of semirigid material is inserted into the lumen of a delivery catheter. The delivery catheter is advanced within the patient until its distal end is located adjacent to the desired insertion site, which is preferably the junction between a coronary artery and passageway formed in the myocardium between the left ventricle and coronary artery. A proximal section of the shunt is first advanced out of the delivery catheter into the myocardial passageway. A distal section of the shunt is advanced into the coronary artery, preferably by advancing the distal section of the shunt into the myocardial passageway and then pulling the distal section back into the coronary artery, or by pushing the distal section of the shunt in a folded configuration out of the delivery catheter into the coronary artery. In one embodiment, the shunt is made of a collapsible material for insertion into the delivery catheter, the shunt expanding upon removal from the delivery catheter.

In one aspect of the present invention, a method of delivering a conduit into a portion of the body having a first passageway and a second passageway joined generally at an angle is provided. A delivery catheter is advanced into the patient, the delivery catheter having a proximal end and a distal end and a lumen extending therethrough. The delivery catheter once advanced has a proximal end that extends outside of the patient and a distal end located substantially adjacent the location where the first passageway and the second passageway are joined. A conduit is inserted into the lumen of the delivery catheter, the conduit having a proximal section and a distal section. The proximal section of the conduit is advanced out of the lumen at the distal end of the delivery catheter into the first passageway. The distal section of the conduit is advanced into the second passageway.

In another aspect of the present invention, a method for creating a bypass between a chamber of the heart and a blood vessel adjacent to that chamber is provided. A passageway is formed in a heart wall that extends between the chamber of the heart and the blood vessel. The passageway has a proximal end opening into the chamber of the heart and a distal end opening into the blood vessel. A conduit is advanced having a proximal end and a distal end through the distal end of the passageway toward its proximal end. The proximal end of the conduit once advanced extends past the heart wall into the chamber of the heart, and the distal end of the conduit once advanced is located in the heart wall. The distal end of the conduit is advanced out of the distal end of the passageway and into the blood vessel downstream of the passageway.

In another aspect of the present invention, a method for creating a bypass between a chamber of the heart and a blood vessel adjacent to that chamber is provided. A passageway is formed in the heart wall that extends between the chamber of the heart and the blood vessel. The passageway has a proximal end opening into the chamber of the heart and a distal end opening into the blood vessel. A conduit having a proximal end and a distal end is folded to define a proximal section and a distal section between the fold. The folded conduit is inserted into a delivery catheter having a proximal end and a distal end and a lumen extending therethrough. The conduit is inserted such that the proximal end of the conduit is nearer to the distal end of the delivery catheter than the distal end of the conduit is to the distal end of the delivery catheter. Both the proximal end and the distal end of the conduit face toward the distal end of the delivery catheter. The delivery catheter is advanced into a patient into the blood vessel until its distal end is adjacent to the distal end of the passageway in the heart wall. The proximal section of the conduit is advanced out of the lumen at the distal end of the delivery catheter into the passageway. The distal section of the conduit is advanced out of the lumen at the distal end into the blood vessel.

DETAILED DESCRIPTION OF THE PREFERRED EMBODIMENTS

Figure 1A:
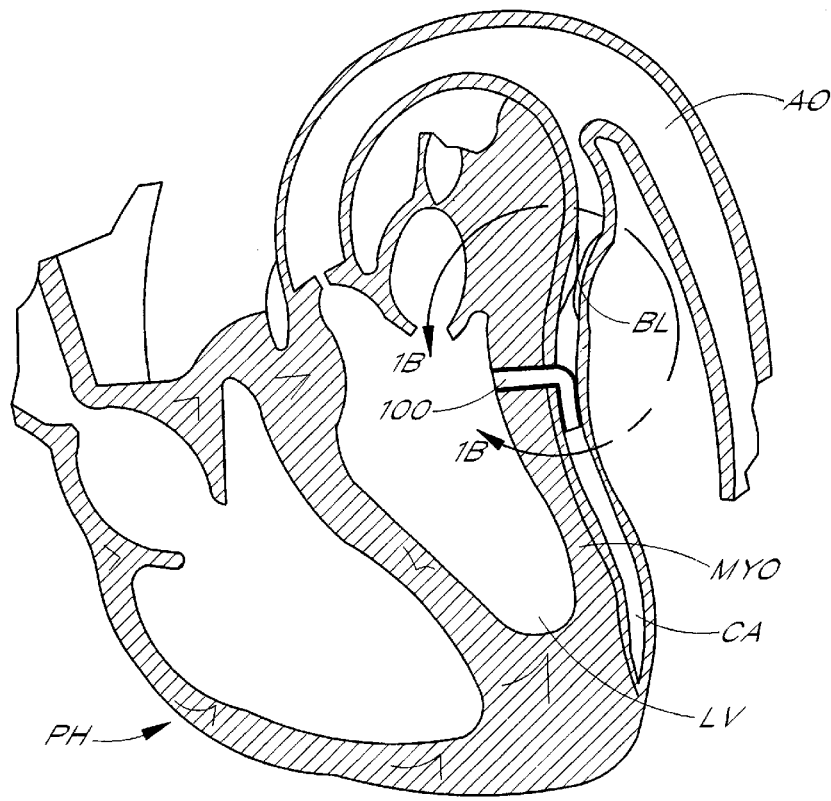
FIG. 1A is a schematic, cross-sectional view of a human heart, showing an L-shaped shunt device in the myocardium of the heart for forming a bypass between the left ventricle and a coronary artery.

The preferred embodiments described hereinbelow depict methods and apparatus for delivering a shunt into the myocardium to create a conduit between the left ventricle and coronary artery. Although the embodiments below describe delivery of an L-shaped shunt, it will be appreciated that these embodiments may also be applied to the delivery of similar types devices such as stents and other devices. Moreover, the methods and apparatus described herein may be used for delivery of these devices into other body tissues and vessels. For example, an L-shaped shunt may be delivered between other heart chambers to other coronary vessels. Although the term "L-shaped" is used herein for convenience, it will be understood that the shunt is merely generally L-shaped. Thus, the "L-shaped" shunt includes shunts that are angled, cornered, or simply change the direction of flow within the shunt from its proximal end to its distal end.

The principles of the present invention are not limited to left ventricular conduits, and include conduits for communicating bodily fluids from any space within a patient to another space within a patient, including any mammal. Furthermore, such fluid communication through the conduits is not limited to any particular direction of flow and can be antegrade or retrograde with respect to the normal flow of fluid. Moreover, the conduits may communicate between a bodily space and a vessel or from one vessel to another vessel (such as an artery to a vein or vice versa). Moreover, the conduits can reside in a single bodily space so as to communicate fluids from one portion of the space to another. For example, the conduits can be used to achieve a bypass within a single vessel, such as communicating blood from a proximal portion of an occluded coronary artery to a more distal portion of that same coronary artery.

In addition, the conduits and related methods can preferably traverse various intermediate destinations and are not limited to any particular flow sequence. Preferred embodiments are disclosed, including direct transmyocardial communication from a left ventricle, through the myocardium and into the coronary artery. The term "transmyocardial" should not be narrowly construed in connection with the preferred fluid communication conduits, and other non-myocardial and even non-cardiac fluid communication are preferred as well. With respect to the walls of the heart (and more specifically the term "heart wall"), the preferred conduits and related methods are capable of fluid communication through all such walls including, without limitation, the pericardium, epicardium, myocardium, endocardium, septum, etc.

The bypass which is achieved with certain preferred embodiments and related methods is not limited to a complete bypass of bodily fluid flow, but can also include a partial bypass which advantageously supplements the normal bodily blood flow. Moreover, the occlusions which are bypassed may be of a partial or complete nature, and therefore the terminology "bypass" or "occlusion" should not be construed to be limited to a complete bypass or a complete occlusion but can include partial bypass and partial occlusion as described.

The preferred conduits and related methods disclosed herein can also provide complete passages or partial passages through bodily tissues. In this regard, the conduits can comprise stents, shunts, or the like, and therefore provide a passageway or opening for bodily fluid such as blood. Moreover, the conduits are not necessarily stented or lined with a device but can comprise mere tunnels or openings formed in the tissues of the patient.

The conduits of the present invention preferably comprise both integral or one-piece conduits as well as plural sections joined together to form a continuous conduit. The preferred conduit device and method for installation is preferably determined by appropriate patient indications in accordance with sound medical practices.

Figure 1B:
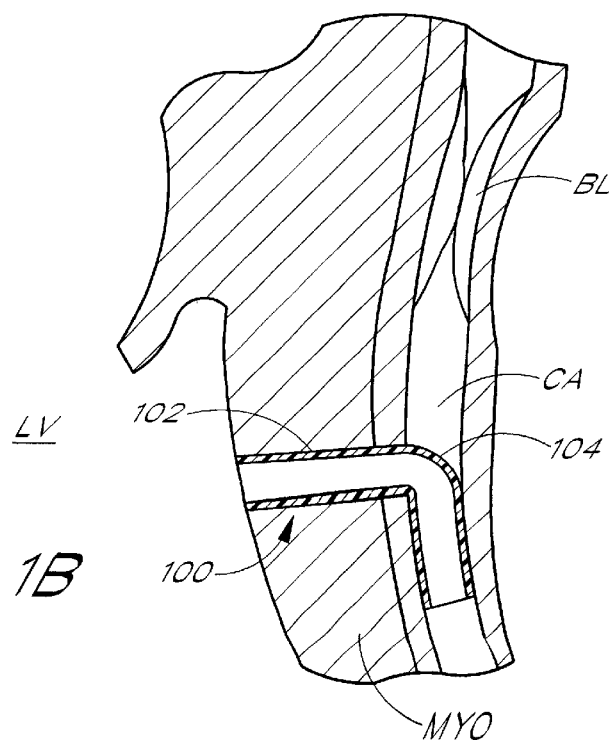
FIG. 1B is an enlarged view of section 1B—1B of the bypass shunt of FIG. 1A.
Figure 2:
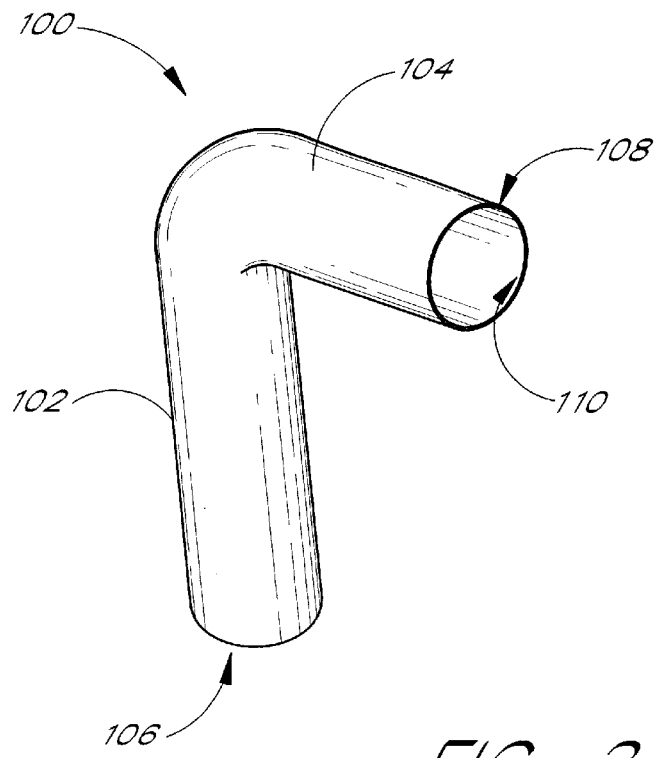
FIG. 2 is a perspective view of an L-shaped shunt according to one embodiment of the present invention.

As illustrated in FIGURES 1A and 1B, a coronary artery bypass is accomplished by disposing a conduit or shunt 100 in a heart wall or myocardium MYO of a patient's heart PH. As shown in FIG. 2, shunt 100 preferably has a first section 102 that extends from the left ventricle LV of heart PH to a clogged coronary artery CA at a point downstream of a blockage BL. Once inside the coronary artery CA, the shunt 100 bends to a second section 104 that extends downstream from the blockage BL. Although not shown in FIGS. 1A and 1B, shunt 100 may also have a one-way valve disposed therein for preventing back flow of blood through shunt, such as described in U.S. Pat. No. 5,429,144, the entirety of which is hereby incorporated by reference.

The shunt 100 illustrated in FIGS. 1A and 1B, and shown more particularly in FIG. 2, is preferably an elongate body having a proximal end 106 and a distal end 108 and a lumen 110 extending therethrough. Shunt 100 is preferably made of a semi-rigid biocompatible material such as a biocompatible polymers, although other materials may also be used. The use of a semi-rigid material allows the shunt 100 to be easily folded into an L-shaped configuration, as shown in FIGURES 1A and 1B and described below. Further details regarding conduits or shunts such as described herein, as well as other medical devices and methods for use with the preferred embodiments of the present invention, are disclosed in copending applications entitled DESIGNS FOR LEFT VENTRICULAR CONDUIT, application Ser. No. 09/369,048 filed the same date herewith, LEFT VENTRICULAR CONDUIT WITH BLOOD VESSEL GRAFT, application Ser. No. 09/369,061, filed the same date herewith, VALVE DESIGNS FOR LEFT VENTRICULAR CONDUITS, application Ser. No. 09/369,393, filed the same date herewith, and LEFT VENTRICULAR CONDUITS TO CORONARY ARTERIES AND METHODS FOR CORONARY BYPASS, application Ser. No. 09/369,039, filed the same date herewith, as well as U.S. Pat. Nos. 5,662,124, 5,429,144 and 5,755,682, all of which are hereby incorporated by reference in their entirety.

Passageway Formation

In one preferred embodiment of the present invention, before delivery of the shunt 100, a passageway is formed at a desired location within the patient for placement of the shunt 100 within the patient. Although the formation of this passageway is described in a percutaneous approach, it will also be appreciated that surgical and other methods may be used as well.

Figure 3:
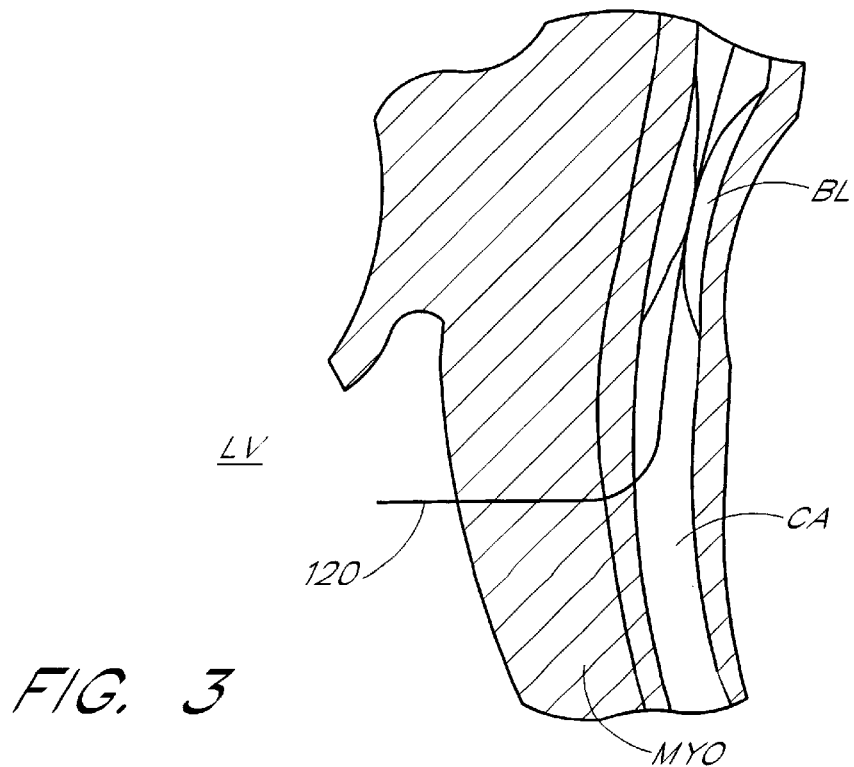
FIG. 3 is a schematic partial cross-sectional view of a coronary artery adjacent the left ventricle, showing a guidewire being advanced through an obstruction in the coronary artery.
Figure 4:
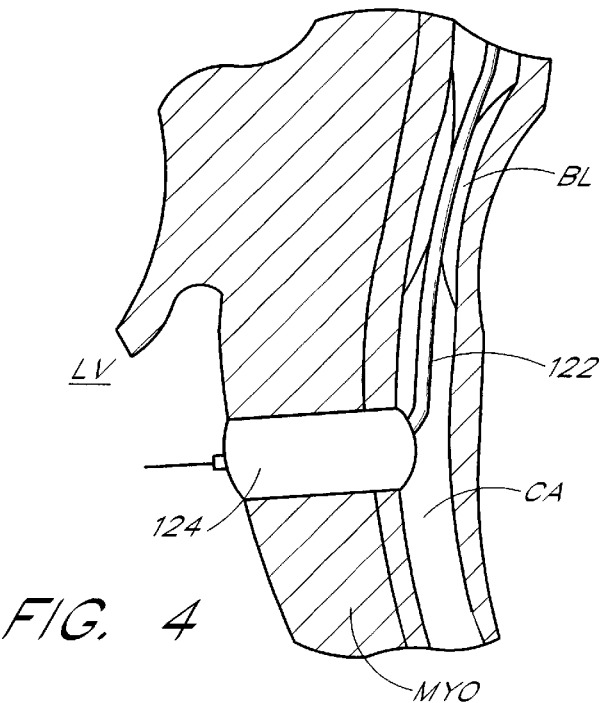
FIG. 4 is a schematic partial cross-sectional view of a coronary artery adjacent the left ventricle, showing a dilation catheter being advanced over the guidewire of FIG. 3 to create a myocardial passageway.
Figure 5:
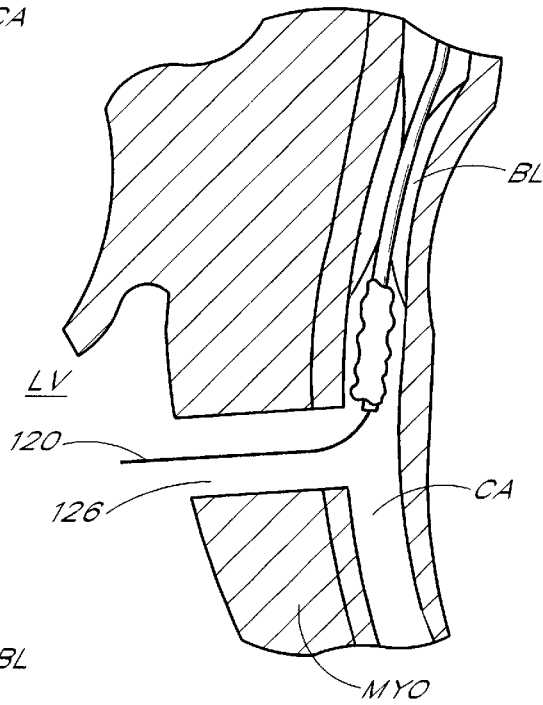
FIG. 5 is a schematic partial cross-sectional view of a coronary artery adjacent the left ventricle, showing the dilation catheter of FIG. 4 being retracted from the myocardium leaving a passageway through the myocardium.

FIGS. 3–5 illustrate the formation of a passageway 126 within the myocardium MYO of a patient extending between the left ventricle LV and the coronary artery CA. As shown in FIG. 3, a guidewire 120 is inserted into the coronary artery CA through the myocardium and into the left ventricle. This guidewire is preferably inserted into the patient through the femoral artery (not shown) and advanced percutaneously through aorta AO (shown in FIG. 1A) and through the blockage BL in the coronary artery, as is well known by those in the art. The guidewire then turns into the myocardium and extends therethrough, where it may be anchored at the left ventricle to the myocardium. Further details regarding these and other delivery methods are described in copending application entitled DELIVERY METHODS FOR LEFT VENTRICULAR CONDUIT, application Ser. No. 09/368,868, filed on the same date as the present application, which is hereby incorporated by reference in its entirety.

After delivery of the guidewire 120, a dilation device 122, as shown in FIG. 4, is delivered over the guidewire 120 to open a passageway through the myocardium MYO. This dilation device 122 may employ radiation, lasers, balloons, successfully larger catheters, a surgical drill or other methods to penetrate through the myocardium. FIG. 4 illustrates the use of a catheter 122 having a dilation balloon 124 mounted on the catheter for forming the passageway. The dilation catheter 122 is advanced over the guidewire 120, and the balloon 124 is inflated within myocardium MYO to expand the myocardial passageway 126, shown in FIG. 5. The balloon 124 is then deflated and the catheter 122 removed, as shown in FIG. 5, to leave the passageway 126 extending through the myocardium MYO. The process may be repeated with successively larger dilation balloons to form a passageway of desired size. Further details are described in the above-referenced application entitled DELIVERY METHODS FOR LEFT VENTRICULAR CONDUIT, application Ser. No. 09/368,868, filed on the same date as the present application, the entirety of which is hereby incorporated by reference. It will be appreciated that other methods may also be used to form the passageway 126.

After formation of the passageway 126, the guidewire 120 may be removed for subsequent delivery of the shunt 100, or may remain in place to assist in the delivery as described below. It will be appreciated that other treatments known to one skilled in the art, such as angioplasty, may be used to reduce the size of the blockage BL before delivering the shunt.

Pullback Technique

In one embodiment of the present invention, the L-shaped shunt is delivered using a pullback technique. The term "pullback" is used for convenience only, and is not limited to pulling back only, but includes pushing and pulling of the shunt. According to this embodiment, a delivery catheter 100 is used to deliver the shunt 100 into a myocardial passageway such as formed in FIG. 5, or by any other method.

Figure 6:
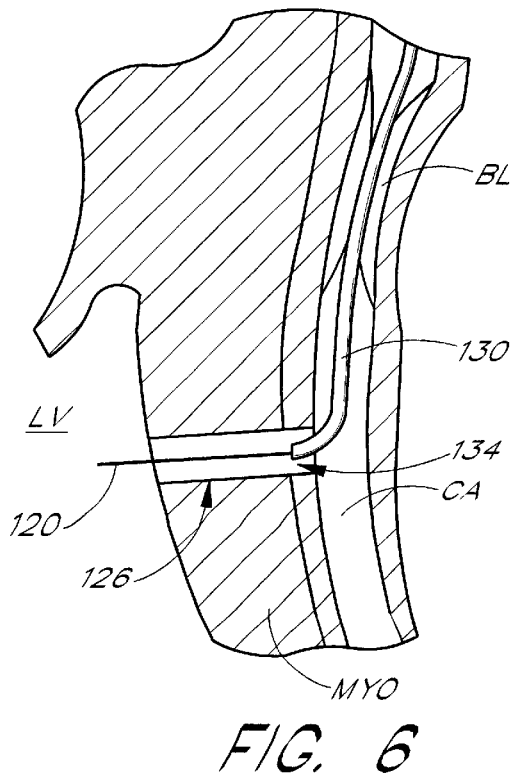
FIG. 6 is a schematic partial cross-sectional view of a coronary artery adjacent the left ventricle, showing a delivery catheter having a distal end positioned at least partially in the myocardial passageway of FIG. 5.

As shown in FIG. 6, a delivery catheter 130 is advanced over a guidewire 120, such as described above, toward the myocardium MYO. The delivery catheter 130 preferably has a proximal end 132 (not shown) extending outside of the patient and a distal end 134 extending at least partially within the passageway 126 formed in the myocardium MYO. More preferably, the distal end 134 of the delivery catheter 130, once delivered as shown in FIG. 6, turns into the passageway 126 so that the lumen 136 (not shown) of the delivery catheter faces into the passageway 126. After the delivery catheter has been placed in this position, the guidewire 120 may be removed to prevent interference with subsequent delivery of the shunt.

Figure 7:
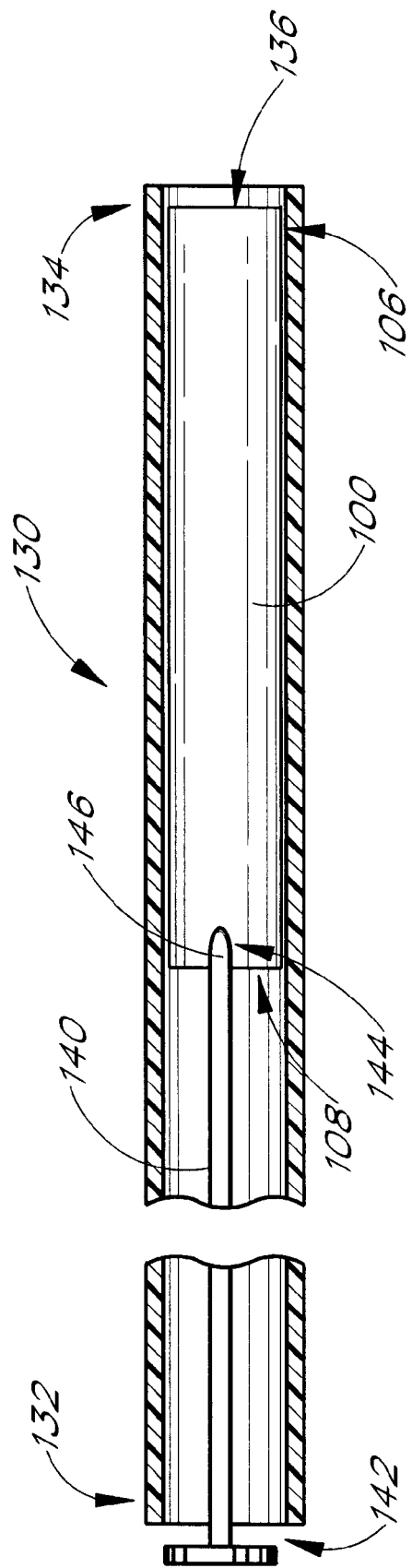
FIG. 7 is a partial cross-sectional view of the delivery catheter of FIG. 6 having a shunt inserted therein.

The shunt 100 is prepared for delivery into the passageway 126 by inserting the shunt into the delivery catheter 130. As shown in FIG. 7, the shunt 100 is inserted into the lumen 136 in a substantially linear configuration, and is positioned near the distal end 134 of the delivery catheter 130. In one embodiment, the shunt 100 is preferably collapsible within the lumen 136 so that it has a collapsed dimension for insertion smaller than its expanded dimension when implanted in the patient. The shunt 100 is positioned in the lumen 136 preferably so that the proximal end 106 of the shunt is nearest to the distal end 134 of the delivery catheter, and the distal end 108 of the shunt is nearest to the proximal end 132 of the delivery catheter.

As shown in FIG. 7, a positioning rod 140 assists insertion and positioning of the shunt 100 within the lumen 136 of the delivery catheter. This rod 140 is preferably an elongate body having a proximal end 142 and a distal end 144, and is made of a material with sufficient stiffness to be pushable through the lumen of the delivery catheter 100 without bending back on itself. Moreover, the rod 140 also has sufficient flexibility so that it can bend and navigate through the pathways of the human vasculature. Suitable materials for the rod 140 include biocompatible materials such as nitinol, stainless steel and polymers.

The distal end of the rod 140 is provided with a grasper or clasp 146 for holding the distal end 108 of the shunt 100. More particularly, the clasp 146 is attached to the shunt 100 prior to insertion of the shunt into the delivery catheter. The shunt 100 is preferably delivered by inserting the shunt into the proximal end 132 of the delivery catheter, and pushing distally on the rod 140 outside of the patient until the shunt is at the distal end of the delivery catheter. It will also be appreciated that the shunt 100 may be inserted into the delivery catheter before the delivery catheter is advanced into the patient, either by pushing the shunt through the proximal end of the delivery catheter or by pulling the shunt through the distal end of the delivery catheter.

Figure 8:
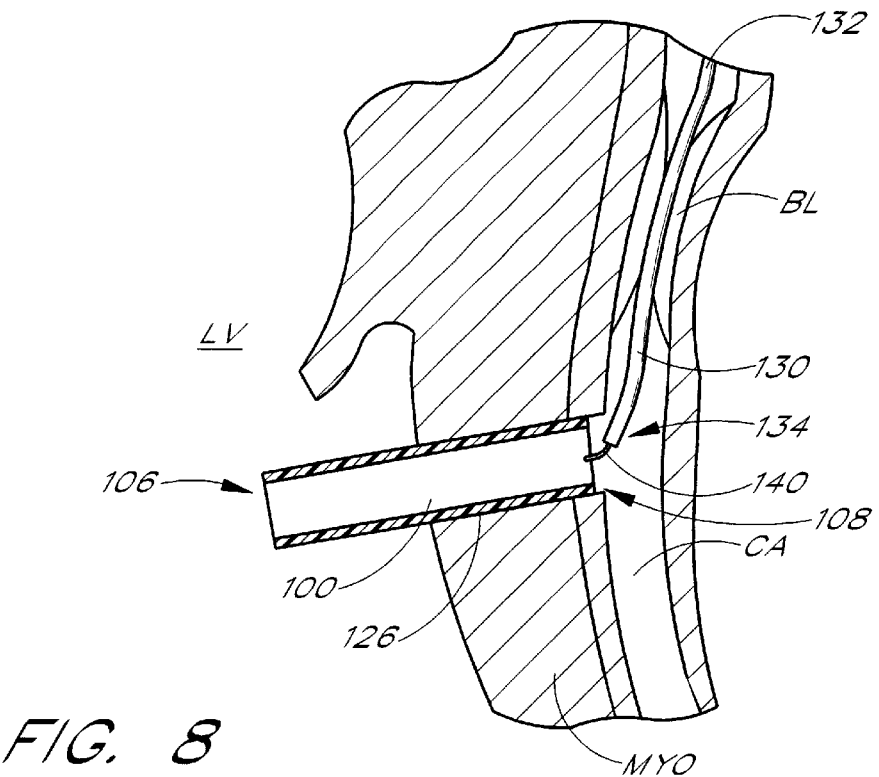
FIG. 8 is a schematic partial cross-sectional view of a coronary artery adjacent the left ventricle, showing a delivery catheter delivering a shunt into the myocardial passageway of FIG. 5.

As shown in FIG. 8, once the shunt 100 is at the distal end 134 of the delivery catheter 130, with the distal end 134 turned at least partially into the passageway 126, the rod 140 is pushed distally to advance the shunt 100 out of the lumen 136 and into the passageway 126. The shunt 100 is preferably constructed from a material having sufficient pushability not only to enable pushing of the shunt through the lumen of the delivery catheter, but also through the passageway 126 formed in the myocardium MYO. It will be appreciated that when the shunt 100 is collapsible within lumen 136, removal of the shunt 100 from the delivery catheter 130, causes the shunt to expand to a size that substantially fills the myocardial passageway 126, as shown in FIG. 8. The rod 140 preferably pushes the shunt 100 completely out of the distal end 134 of the delivery catheter, with the proximal end 106 of the shunt 100 extending past the myocardial wall and into the left ventricle LV. More preferably, the proximal end 106 extends into the left ventricle LV by approximately the distance desired for the section 104 to extend into the coronary artery, as shown in FIG. 1B.

Figure 9:
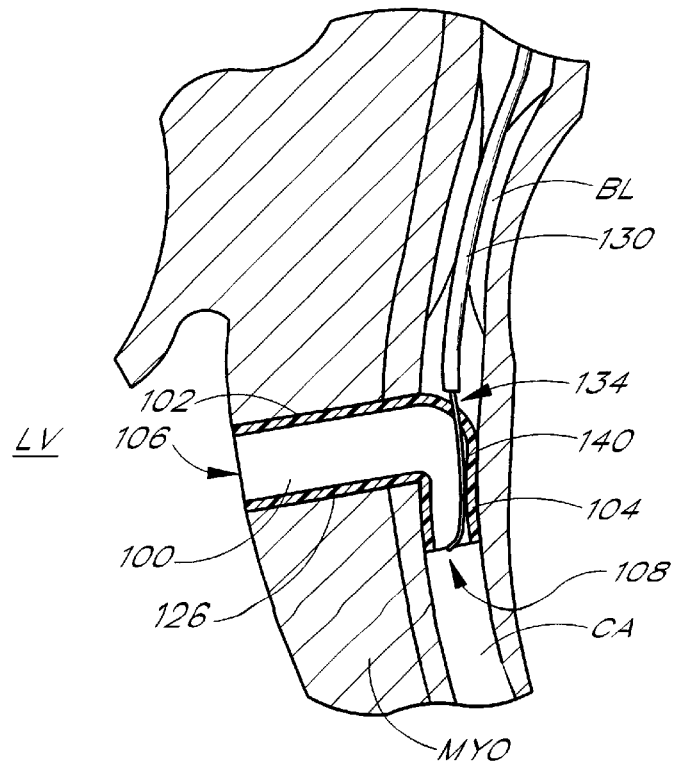
FIG. 9 is a schematic partial cross-sectional view of a coronary artery adjacent the left ventricle, showing the formation of an L-shaped shunt between the left ventricle and coronary artery.

As shown in FIG. 9, the delivery catheter 130 is then preferably pulled back proximally of the passageway 126 so that the lumen 136 at the distal end 134 faces downstream in the coronary artery CA rather than into the passageway 126. The rod 140 is then pulled back proximally to move the distal end 108 of the shunt 100 out of the passageway 126 and into the coronary artery CA. Because the lumen 136 of the delivery catheter faces into the coronary artery CA, pushing distally on the rod 140 as shown in FIG. 9, causes the shunt 100 to bend around the corner between the passageway 126 and the coronary artery CA. The rod 140 is pushed distally until the proximal end 106 of the shunt 100 is substantially flush with the myocardial wall at the left ventricle LV, and the distal end 108 of the shunt 100 lies in the coronary artery CA downstream from the passageway 126. Because in the preferred embodiment the shunt 100 is collapsible, the shunt 100 does not interfere with pushing of the rod 140 downstream into the coronary artery CA.

After the shunt 100 is positioned as described above, the clasp 146 on the rod 140 is actuated at the proximal end of the rod 140 by an operator, outside of the patient, to release the shunt. The rod 140 and delivery catheter 130 are then retracted from the body, leaving the L-shaped shunt in place for a bypass between the left ventricle LV and the coronary artery CA. As implanted, the shunt 100 has a proximal section 102 within the myocardial passageway 126 and a distal section 104 within the coronary artery CA, such as shown in FIG. 1B.

Folded Shunt Technique

Figure 10:
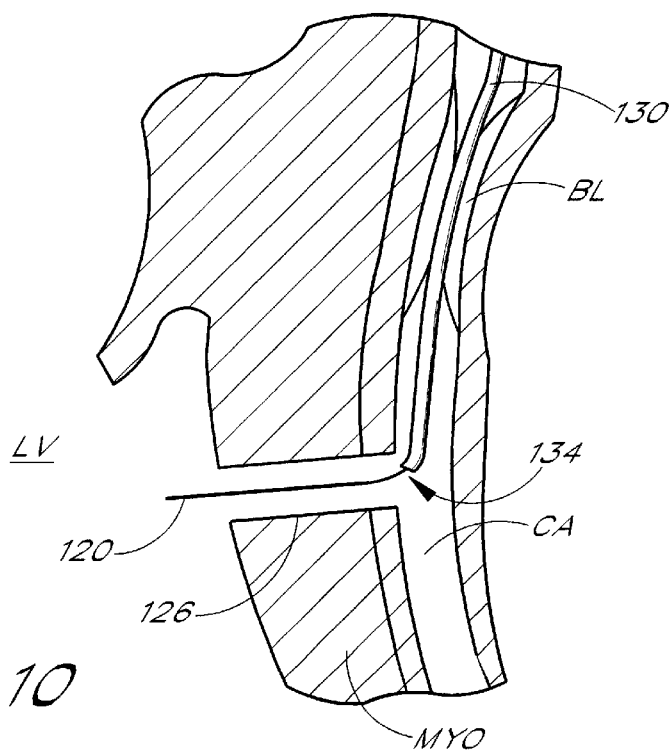
FIG. 10 is a schematic partial cross-sectional view of a coronary artery adjacent the left ventricle, showing a delivery catheter facing partially into the myocardial passageway of FIG. 5 and partially downstream into the coronary artery.

FIG. 10 illustrates another embodiment for delivering an L-shaped shunt into the passageway 126 formed in the myocardium MYO. As with the embodiment shown in FIG. 6, a delivery catheter 130 having a proximal end 132 and a distal end 134 and a lumen 136 (not shown) extending therethrough is advanced over a guidewire 120 toward the passageway 126. Preferably, the delivery catheter 130 is advanced until the distal end 134 extends partially into the passageway 126, such that the lumen 136 at the distal end faces at least partially into the passageway 126. Once the delivery catheter is placed in this position, the guidewire 120 is preferably removed.

Figure 11:
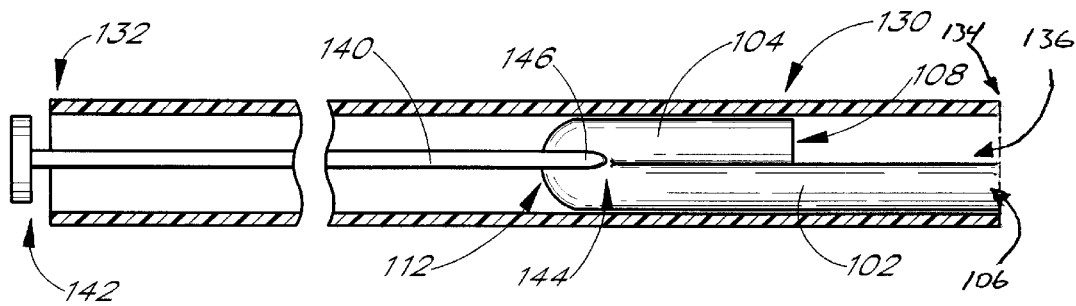
FIG. 11 is a partial cross-sectional view of the delivery catheter of FIG. 10 having a folded shunt inserted therein.

A shunt 100 is positioned at the distal end 134 of the delivery catheter 130 in the lumen 136. As shown in FIG. 11, this shunt is inserted into the catheter and preferably collapsed, such that its proximal end 106 is closest to the distal end 134 of the delivery catheter 130, and its distal end 108 is folded over within the lumen 136. The fold 112 causes the distal end 108 and the proximal end 106 to face in the same distal direction while inserted into the lumen 136 of the delivery catheter. More particularly, the fold 112 in the shunt preferably divides the shunt into a proximal section 102, which is to extend into the passageway 126, and a distal section 104, which is to extend into the coronary artery CA. The location of fold 112 is preferably determined by the length of the passageway 126, and more particularly, is placed such that the proximal section 102 has a length substantially corresponding with the length of the passageway 126.

As described with respect to the pullback technique above, the shunt 100 is preferably collapsible within lumen 136. More preferably, the shunt 100 may be made of a shape memory material such as nitinol to give the shunt 100 a remembered expanded shape such as shown in FIG. 2. In this embodiment, the shunt 100 is collapsed within the lumen 136 from the expanded shape for insertion into the patient.

The folded shunt 100 is preferably loaded into the delivery catheter through use of rod 140, as illustrated in FIG. 11. This rod 140 is similar to the rod described with respect to FIG. 7 above, more particularly having a proximal end 142 and a distal end 144. A clasp 146 is provided at the distal end of the rod 140, which grasps the shunt 100 at about the fold 112. The shunt 100 is preferably loaded into the delivery catheter 130 through the proximal end 132 after the delivery catheter has reached its position shown in FIG. 11 by pushing distally on the rod 140 which is attached to the shunt 100. It will be appreciated, however, that the shunt may be loaded prior to inserting the delivery catheter 130 into the patient, either by pushing through the proximal end 132 or pulling through the distal end 134.

Figure 12:
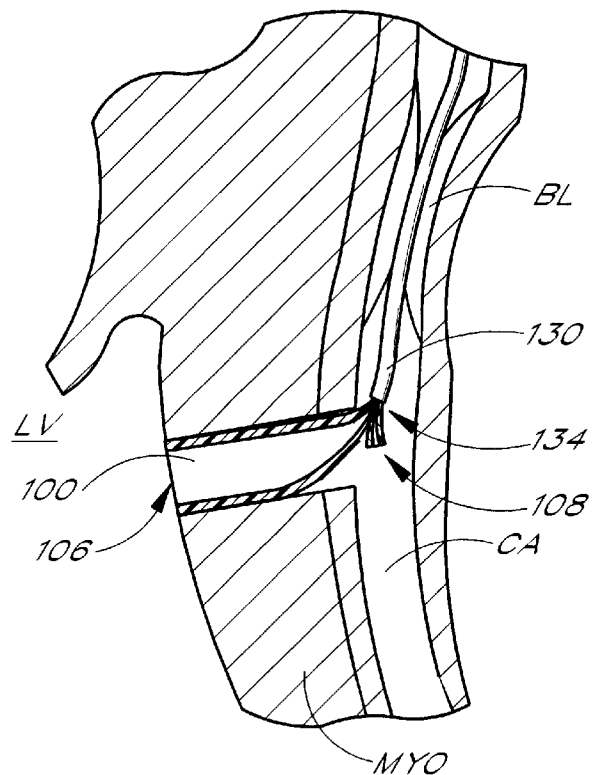
FIG. 12 is a schematic partial cross-sectional view of a coronary artery adjacent the left ventricle, showing a delivery catheter delivering the proximal section of an L-shaped shunt into the myocardial passageway of FIG. 5.

Once the shunt 100 has reached the distal end 134 of the delivery catheter 130, the delivery catheter is turned, if necessary, to ensure that the proximal section 102 of the shunt 100 is in the part of the lumen 136 closest to the passageway 126. With the distal end of the delivery catheter facing at least partially into the passageway 126, when the rod 140 is pushed distally to advance the shunt 100 out of the delivery catheter 130, this positioning causes the proximal section 102 of the shunt to exit the delivery catheter first into the passageway 126, as shown in FIG. 12. As the proximal section 102 exits the lumen 136, the shunt 100 begins to expand toward its expanded shape.

Figure 13:
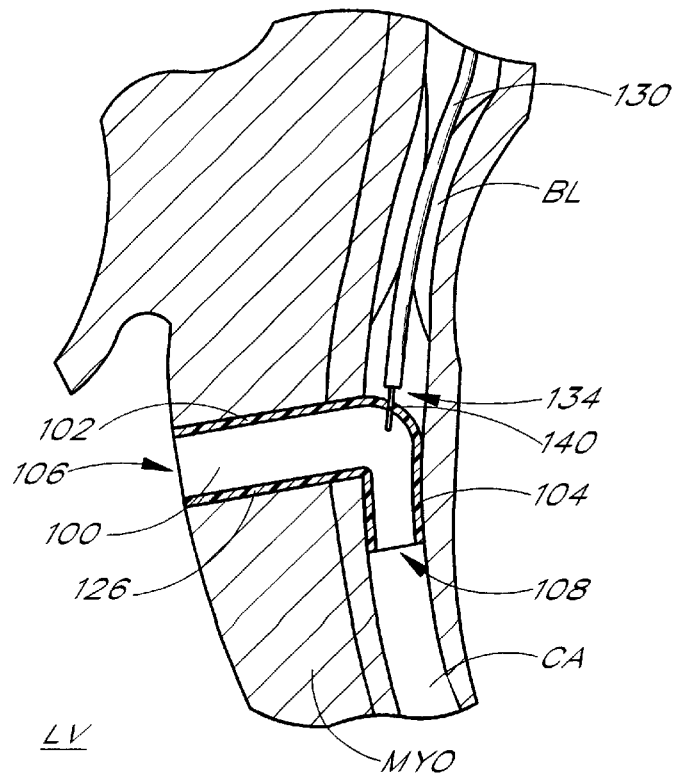
FIG. 13 is a schematic partial cross-sectional view of a coronary artery adjacent the left ventricle, showing a delivery catheter delivering the distal section of an L-shaped shunt into the coronary artery.

As the rod 140 pushes the shunt 100 further distally out of the delivery catheter 130, the distal section 104 of the shunt exits into the coronary artery CA because of the placement of the distal section 104 within the lumen 136 away from the myocardium. In one embodiment, when the delivery catheter 130 is delivered, the lumen 136 of the distal end 134 faces partially into the passageway 126, and partially into the coronary artery CA, as shown in FIG. 10. Then, because the catheter 130 is turned, as necessary, to position the proximal section 102 of the shunt 100 in the part of the lumen 136 facing the passageway 126, correspondingly, the distal section 104 is positioned in the part of the lumen 136 that faces into the coronary artery CA. This allows the distal section 104 to exit the delivery catheter 130 into the coronary artery CA. To further assist in delivering the distal section 104 into the coronary artery CA, the delivery catheter 130 may be pulled proximally back once the proximal section 102 enters the passageway 126 so that the lumen 136 at the distal end 134 faces only downstream into the coronary artery CA. As shown in FIG. 13, when the distal end of the rod 140 is pushed out of the delivery catheter 130, the proximal section 102 has extended completely through the passageway 126 such that proximal end 106 of the shunt 100 is approximately flush with the myocardial wall at the left ventricle LV. The distal section 104 extends into the coronary artery CA downstream from the passageway 126. Once in this position, the clasp 146 is removed from the shunt 100 and the delivery catheter 130 and rod 140 are removed.

It will be appreciated that the position of the delivery catheter 130 may be moved during delivery of the shunt 100 to ensure that the proximal section 102 is delivered into the passageway 126 and the distal section is delivered into the coronary artery CA. For example, the delivery catheter 130 may be pushed further into the passageway 126 prior to delivering the proximal section of the shunt 100 therein. Then, prior to delivery of the distal section 104, the delivery catheter 130 may be pulled proximally back so that the lumen 136 at the distal end 134 faces downstream into the coronary artery CA.

The embodiments illustrated and described above are provided merely as examples of certain preferred embodiments of the present invention. Other changes and modifications can be made from the embodiments presented herein by those skilled in the art without departure from the spirit and scope of the invention, as defined by the appended claims.

What is claimed is:

1. A method of delivering a conduit into a portion of a patient's body having a first passageway and a second passageway joined generally at an angle, comprising:
   providing a delivery catheter having a proximal end and a distal end and a lumen extending therethrough;
   placing the delivery catheter in the patient such that the proximal end extends outside of the patient and the distal end is located substantially adjacent a location where the first passageway and the second passageway are joined;
   providing a conduit in the lumen of the delivery catheter, the conduit having a proximal section and a distal section;
   advancing the proximal section of the conduit out of the lumen at the distal end of the delivery catheter into the first passageway; and
   advancing the distal section of the conduit into the second passageway,
   wherein the first passageway is a myocardial passageway formed through the myocardium of the heart between the left ventricle and a coronary artery.

2. The method of claim 1, wherein the second passageway is in a portion of the coronary artery downstream from the myocardial passageway.

3. The method of claim 2, wherein the conduit is provided in the lumen at the distal end of the delivery catheter in a substantially linear configuration, the conduit while provided in the lumen having a proximal end located nearer to the distal end of the delivery catheter and a distal end located nearer to the proximal end of the delivery catheter.

4. The method of claim 3, further comprising, after advancing the proximal section of the conduit out of the lumen into the myocardial passageway, advancing the distal section of the conduit into the myocardial passageway such that the conduit is substantially completely outside of the lumen of the delivery catheter and the proximal end of the conduit extends into the left ventricle.

5. The method of claim 4, wherein advancing the distal section of the conduit into the second passageway comprises moving the distal section out of the myocardial passageway and into the coronary artery.

6. The method of claim 2, wherein the conduit is provided in the lumen at the distal end in a folded configuration, wherein the distal section of the conduit is folded over the proximal section, the conduit having a proximal end and a distal end that both face the distal end of the delivery catheter, the proximal end of the conduit being located closer to the distal end of the delivery catheter than the distal end of the conduit is located to the distal end of the delivery catheter.

7. The method of claim 6, wherein the proximal section of the conduit is advanced into the first passageway by pushing the conduit out of the lumen.

8. The method of claim 7, wherein the distal section of the conduit is advanced into the second passageway by pushing the conduit out of the lumen.

9. The method of claim 1, further comprising collapsing the conduit prior to providing the conduit in the lumen.

10. The method of claim 1, wherein, prior to advancing the proximal section out of the delivery catheter, the delivery catheter is placed such that the lumen at the distal end faces at least partially into the first passageway.

11. The method of claim 1, further comprising forming the first passageway.

12. The method of claim 11, wherein forming the passageway includes inserting a dilation mechanism into the myocardial wall and dilating the myocardial wall.

13. The method of claim 12, wherein the dilation mechanism is a balloon and dilating the myocardial wall includes inflating the balloon.

14. The method of claim 1, further comprising, prior to advancing the conduit into the first passageway, releasably attaching a rod to the conduit.

15. The method of claim 14, wherein advancing the conduit into the first passageway comprises pushing the rod distally to move the conduit out of the lumen.

16. The method of claim 14, wherein advancing the conduit out of the distal end of the lumen and into the second passageway comprises pushing the rod into the second passageway.

17. The method of claim 1, further comprising positioning the delivery catheter such that the distal end of the lumen faces at least partially toward the first passageway while advancing the proximal section of the conduit into the first passageway.

18. The method of claim 1, further comprising positioning the delivery catheter such that the distal end of the lumen substantially faces downstream in the coronary artery while advancing the distal section of the conduit into the second passageway.

19. The method of claim 1, wherein the conduit is made of a shape memory material having a collapsible shape when provided in the delivery catheter and an expanded shape when advanced into the first passageway and into the second passageway.

20. The method of claim 1, wherein placing the delivery catheter includes advancing the delivery catheter through a blood vessel.

21. A method of delivering a conduit into a portion of a patient's body having a first passageway and a second passageway joined generally at an angle, comprising:
   forming the first passageway;
   providing a delivery catheter having a proximal end and a distal end and a lumen extending therethrough;
   placing the delivery catheter in the patient such that the proximal end extends outside of the patient and the distal end is located substantially adjacent a location where the first passageway and the second passageway are joined;
   providing a conduit in the lumen of the delivery catheter, the conduit having a proximal section and a distal section;

advancing the proximal section of the conduit out of the lumen at the distal end of the delivery catheter into the first passageway; and advancing the distal section of the conduit into the second passageway, wherein the first passageway is formed in a myocardial wall of a heart between a heart chamber and a blood vessel, and the second passageway is in the blood vessel.

22. The method of claim 21, wherein the dilation mechanism is a balloon and dilating the myocardial wall includes inflating the balloon.

23. The method of claim 22, wherein the dilation mechanism is a balloon and dilating the myocardial wall includes inflating the balloon.

24. The method of claim 21, wherein the second passageway is in a portion of the blood vessel downstream from the myocardial passageway.

25. The method of claim 24, wherein the conduit is provided in the lumen at the distal end of the delivery catheter in a substantially linear configuration, the conduit while provided in the lumen having a proximal end located nearer to the distal end of the delivery catheter and a distal end located nearer to the proximal end of the delivery catheter.

26. The method of claim 25, further comprising, after advancing the proximal section of the conduit out of the lumen into the myocardial passageway, advancing the distal section of the conduit into the myocardial passageway such that the conduit is substantially completely outside of the lumen of the delivery catheter and the proximal end of the conduit extends into the heart chamber.

27. The method of claim 26, wherein advancing the distal section of the conduit into the second passageway comprises moving the distal section out of the myocardial passageway and into the blood vessel.

28. The method of claim 24, wherein the conduit is provided in the lumen at the distal end in a folded configuration, wherein the distal section of the conduit is folded over the proximal section, the conduit having a proximal end and a distal end that both face the distal end of the delivery catheter, the proximal end of the conduit being located closer to the distal end of the delivery catheter than the distal end of the conduit is located to the distal end of the delivery catheter.

29. The method of claim 28, wherein the proximal section of the conduit is advanced into the first passageway by pushing the conduit out of the lumen.

30. The method of claim 26, wherein the distal section of the conduit is advanced into the second passageway by pushing the conduit out of the lumen.

31. The method of claim 21, wherein, prior to advancing the proximal section out of the delivery catheter, the delivery catheter is placed such that the lumen at the distal end faces at least partially into the first passageway.

32. The method of claim 21, wherein placing the delivery catheter includes advancing the delivery catheter through a blood vessel.

33. A method of delivering a conduit into a portion of a patient's body having a first passageway and a second passageway joined generally at an angle, comprising:

providing a delivery catheter having a proximal end and a distal end and a lumen extending therethrough;

placing the delivery catheter in the patient such that the proximal end extends outside of the patient and the distal end is located substantially adjacent a location where the first passageway and the second passageway are joined;

providing a conduit in the lumen of the delivery catheter, the conduit having a proximal section and a distal section;

advancing the proximal section of the conduit out of the lumen at the distal end of the delivery catheter into the first passageway; and advancing the distal section of the conduit into the second passageway, wherein delivering the conduit includes creating a bypass between a chamber of a heart and a blood vessel adjacent to the chamber.

34. The method of claim 33, wherein the first passageway is a myocardial passageway formed through the myocardium of the heart between a left ventricle and a coronary artery.

35. The method of claim 34, wherein the second passageway is in a portion of the coronary artery downstream from the myocardial passageway.

36. The method of claim 35, wherein the conduit is provided in the lumen at the distal end of the delivery catheter in a substantially linear configuration, the conduit while provided in the lumen having a proximal end located nearer to the distal end of the delivery catheter and a distal end located nearer to the proximal end of the delivery catheter.

37. The method of claim 36, further comprising, after advancing the proximal section of the conduit out of the lumen into the myocardial passageway, advancing the distal section of the conduit into the myocardial passageway such that the conduit is substantially completely outside of the lumen of the delivery catheter and the proximal end of the conduit extends into the left ventricle.

38. The method of claim 37, wherein advancing the distal section of the conduit into the second passageway comprises moving the distal section out of the myocardial passageway and into the coronary artery.

39. The method of claim 35, wherein the conduit is provided in the lumen at the distal end in a folded configuration, wherein the distal section of the conduit is folded over the proximal section, the conduit having a proximal end and a distal end that both face the distal end of the delivery catheter, the proximal end of the conduit being located closer to the distal end of the delivery catheter than the distal end of the conduit is located to the distal end of the delivery catheter.

40. The method of claim 39, wherein the proximal section of the conduit is advanced into the first passageway by pushing the conduit out of the lumen.

41. The method of claim 40, wherein the distal section of the conduit is advanced into the second passageway by pushing the conduit out of the lumen.

42. The method of claim 33, wherein, prior to advancing the proximal section out of the delivery catheter, the delivery catheter is placed such that the lumen at the distal end faces at least partially into the first passageway.

43. The method of claim 33, wherein placing the delivery catheter includes advancing the delivery catheter through a blood vessel.

44. The method of claim 33, further comprising forming the first passageway.

45. The method of claim 44, wherein the heart chamber is a left ventricle and the blood vessel is a coronary artery, and the first passageway is formed in a myocardial wall of a heart between the left ventricle and the coronary artery, and the second passageway is in the coronary artery.

46. A method of delivering a conduit into a portion of a patient's body having a first passageway and a second passageway joined generally at an angle, comprising:

providing a delivery catheter having a proximal end and a distal end and a lumen extending therethrough;

placing the delivery catheter in the patient such that the proximal end extends outside of the patient and the distal end is located substantially adjacent a location where the first passageway and the second passageway are joined;

providing a conduit in the lumen of the delivery catheter, the conduit having a proximal section and a distal section;

releasably attaching a rod to the conduit;

advancing the proximal section of the conduit out of the lumen at the distal end of the delivery catheter into the first passageway; and advancing the distal section of the conduit into the second passageway by pushing the rod into the second passageway.

47. The method of claim 46, wherein the first passageway is a myocardial passageway formed through the myocardium of the heart between the left ventricle and a coronary artery.

48. The method of claim 47, wherein the second passageway is in a portion of the coronary artery downstream from the myocardial passageway.

49. The method of claim 48, wherein the conduit is provided in the lumen at the distal end of the delivery catheter in a substantially linear configuration, the conduit while provided in the lumen having a proximal end located nearer to the distal end of the delivery catheter and a distal end located nearer to the proximal end of the delivery catheter.

50. The method of claim 49, further comprising, after advancing the proximal section of the conduit out of the lumen into the myocardial passageway, advancing the distal section of the conduit into the myocardial passageway such that the conduit is substantially completely outside of the lumen of the delivery catheter and the proximal end of the conduit extends into the left ventricle.

51. The method of claim 50, wherein advancing the distal section of the conduit into the second passageway comprises moving the distal section out of the myocardial passageway and into the coronary artery.

52. The method of claim 48, wherein the conduit is provided in the lumen at the distal end in a folded configuration, wherein the distal section of the conduit is folded over the proximal section, the conduit having a proximal end and a distal end that both face the distal end of the delivery catheter, the proximal end of the conduit being located closer to the distal end of the delivery catheter than the distal end of the conduit is located to the distal end of the delivery catheter.

53. The method of claim 52, wherein the proximal section of the conduit is advanced into the first passageway by pushing the conduit with the rod out of the lumen.

54. The method of claim 46, wherein, prior to advancing the proximal section out of the delivery catheter, the delivery catheter is placed such that the lumen at the distal end faces at least partially into the first passageway.

55. The method of claim 46, wherein placing the delivery catheter includes advancing the delivery catheter through a blood vessel.

56. The method of claim 46, further comprising forming the first passageway.

57. The method of claim 56, wherein the first passageway is formed in a myocardial wall of a heart between a heart chamber and a blood vessel, and the second passageway is in the blood vessel.

\* \* \* \* \*

UNITED STATES PATENT AND TRADEMARK OFFICE
CERTIFICATE OF CORRECTION

PATENT NO. : 6,302,892 B1
DATED : October 16, 2001
INVENTOR(S) : Peter J. Wilk

It is certified that error appears in the above-identified patent and that said Letters Patent is hereby corrected as shown below:

Column 11,
Lines 10-12, delete claim 22, and replace it with the following:

-- 22. The method of claim 21, wherein forming the passageway includes inserting a dilation mechanism into the myocardial wall and dilating the myocardial wall. --;
Line 48, replace "claim 26" with -- claim 29 --.

Signed and Sealed this

Eighteenth Day of June, 2002

Attest:

JAMES E. ROGAN
Attesting Officer      Director of the United States Patent and Trademark Office